United States Patent [19]

Thoma

[11] 4,034,742

[45] July 12, 1977

[54] APPARATUS FOR MECHANICALLY ASSISTING CIRCULATION OF THE BLOOD IN THE HUMAN BODY

[76] Inventor: Herwig Thoma, 40/5, Maroltingergasse, Vienna, Austria

[21] Appl. No.: 651,874

[22] Filed: Jan. 23, 1976

Related U.S. Application Data

[63] Continuation-in-part of Ser. No. 436,226, Jan. 24, 1974, abandoned.

[30] Foreign Application Priority Data

Jan. 31, 1973 Austria ................................ 850/73

[51] Int. Cl.$^2$ ...................... A61M 1/03; A61F 1/24
[52] U.S. Cl. ...................................... 128/1 D; 3/1.7
[58] Field of Search ............. 3/1.7; 128/1 D, 214 R

[56] References Cited

U.S. PATENT DOCUMENTS

| | | | |
|---|---|---|---|
| 3,410,263 | 11/1968 | McGinnis | 128/1 D |
| 3,553,736 | 1/1971 | Kantrowitz et al. | 3/1.7 |
| 3,692,018 | 9/1972 | Goetz et al. | 128/1 D |
| 3,766,567 | 10/1973 | Kahn et al. | 3/1.7 |
| 3,939,820 | 2/1976 | Grayzel | 128/1 D |

FOREIGN PATENT DOCUMENTS 1,503,906   10/1967   France ...................................... 3/1.7

OTHER PUBLICATIONS

Petrovsky et al. – Jour. Thorac. & Card. Surg., vol. 57, No. 3, Mar. 1969, pp. 435–441.
Sharp et al. Trans. Amer. Soc. Artific. Inter. Orgs., 1970 – pp. 435–438.

Primary Examiner—Dalton L. Truluck
Attorney, Agent, or Firm—John C. Smith, Jr.

[57] ABSTRACT

Apparatus for mechanically assisting circulation of the blood in the human body comprises a pumping chamber outside the cardiovascular system of a patient but communicating with said system through only one connection, and means for blocking the backflow of blood from the pumping chamber into the cardiovascular system. The blocking means may be one or more variable flow resistant devices or valves which are suitably located inside the cardiovascular system and controlled to operate in synchronism with the heart beat.

22 Claims, 5 Drawing Figures 4,034,742

APPARATUS FOR MECHANICALLY ASSISTING CIRCULATION OF THE BLOOD IN THE HUMAN BODY

This is a continuation-in-part of copending application Ser. No. 436,226 filed Jan. 24, 1974 now abandoned.

BACKGROUND OF THE INVENTION

This invention relates to apparatus for mechanically assisting circulation of the blood in the human body. The apparatus comprises a pumping chamber in association with a variable flow resistant device or valve directly in the cardiovascular system. According to the invention the apparatus is so positioned in the cardiovascular system that a fully effective pump is formed with the help of the valve functions of the cardiovascular system itself.

Various devices for mechanically assisting circulation of the blood in the human body have been developed in the course of the last twenty years. A primary feature of all these devices is that the diseased heart remains in the body and that its functions are taken over by the assisting device either in toto or more usually only in part (Wolner E.:-Die mechanische Kreislaufunterstutzung in Experiment und Klinik. Weiner klinische Wochenschrift, 84, No. 26, 1972).

From a functional point of view two types of apparatus can be distinguished, namely parallel and series (by-pass and series pass) pumps. The former are parallel to a part of the heart (right or left chamber), the latter are in series therewith. If the whole of the heart is short-circuited (total by-pass) then it is necessary at the same time to reoxygenate the blood because the pulmonary circulation is by-passed. Short period total by-pass has been practiced for many years in cardiac surgery. All these pumps have two openings for the blood stream, viz. an entry and an exit. Some move the blood through valves, others by direct displacement (pinch pumps, roller pumps) in a desired direction. The alternative principle of counterpulsation provides mechanical circulatory relief. Since the heart has a period of rest after each period of work, it is possible during the work period, i.e., during blood ejection (systole) to relieve the pressure in the cardiovascular system, and to introduce energy into the system, i.e., raise the pressure during the period of rest (diastole). This relieves the heart during systole, whereas the required pressure for circulation is mechanically generated during diastole. The particular advantage of counterpulsation is less the relief afforded to the heart than the possibility of properly filling the coronary vessels during diastole. Disregarding short period temporary employment of the total by-pass, i.e., of the heart-lung machine, it can be generally said that circulating pumps are not at present in clinical use, but that the principle of counterpulsation is being employed to an increasing extent.

A major reason for this development is the difficulty of application of the pump because two connections (anastomoses) with the cardiovascular system are needed, whereas in counterpulsation only one of such connection is necessary.

The disadvantage of counterpulsation is the described limited degree of relief afforded to the heart because the pressure in the circulating system may not be arbitrarily reduced during systole. The object of the present invention is to overcome this disadvantage.

SUMMARY OF THE INVENTION

The present invention provides an apparatus for mechanically assisting circulation of the blood in the human body. The apparatus comprises a pumping chamber arranged outside the cardiovascular system of a patient which communicates with the system through only one connection, and means adapted to be positioned in the cardiovascular system to control the pumping chamber in synchronism with the heart beat.

A Dacron graft through the right second intercostal space connects the ascending aorta to the subcutaneously implanted elipsoidal-shaped artificial ventricle. A spherical polyurethane balloon is positioned in the aorta distal to the Dacron graft via the femoral artery. The ventricle and balloon are pneumatically driven synchronously with the EKG. In natural systole the balloon is inflated, occluding the aorta, and the artificial ventricle sucks the entire stroke volume. In natural diastole, the balloon deflates and the artificial ventricle ejects the blood to the aorta. With this system the systolic pressure wave is turned 180° to the natural. The system has high hemodynamic efficiency: the left ventricular systolic pressure is unloaded by 90%, the pump maintains a normal systemic pressure, and the coronary artery flow is increased 5%.

BRIEF DESCRIPTION OF THE DRAWINGS

The invention will now be described by way of example and with reference to the accompanying drawings, in which.

DESCRIPTION OF THE INVENTION

Figure 1:
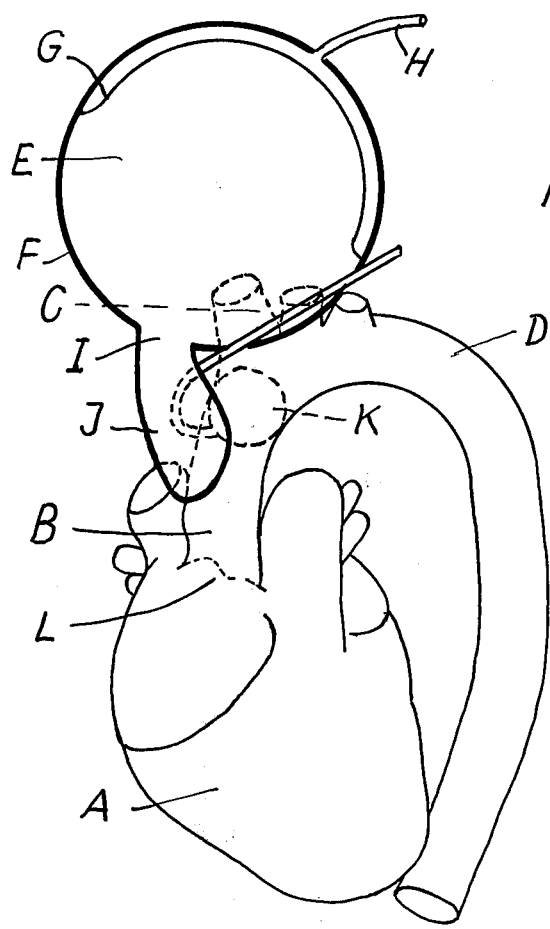
FIG. 1 is a diagram illustrating the working principle of an apparatus according to the invention.

Referring first to FIG. 1, the reference A denotes a heart with its several connecting arteries and veins, B the ascending branch of the aorta, C the arterial branch vessels to the upper part of the body and D the descending branch of the aorta. A mechanical pumping chamber 17 comprises a strong envelope 40 and a movable pumping diaphragm 34 which divides the pumping chamber into upper and lower compartments. The pumping chamber 17 has two connections. The upper compartment of the pumping chamber is cyclically connected to a source of gas pressure and suction (controlled by the heart beat itself) by a pneumatic connection 16. The lower compartment of the pumping chamber is provided with a bottom entry 41 which directly communicates via a connection 25 with the ascending branch B of the aorta. The pressure and suction pulses are transmitted by the movable pumping diaphragm 34 to the lower blood-filled compartment of the pumping chamber and by virtue of the effect of the vacuum this compartment fills with blood during systole. During diastole the pressure in the upper compartment forces the blood out of the lower compartment.

This operation constitutes the working phrase of the pumping chamber.

The functioning of this arrangement is based on the principle of couterpulsation. The apparatus has the particular advantage of being extremely effective because it is located so close to the heart and the pump lumen can be made as large as may be desired.

The pumping action is generated by the cyclic inflation and evacuation of a controlling balloon 22. The systemic circulation is separated from the ventricular exit by the controlling balloon 22 during systole, the balloon performing the function of a variable resistance to the flow of blood. This enables the blood from the heart to enter the pumping chamber 17 practically without back pressure. The controlling balloon could be replaced by a valve which prevent back flow from the aorta. During diastole the controlling balloon collapses and the blood is discharged from the pumping chamber into the arteries. It will be apparent that in this arrangement the semi-lunar valve L (arotic valve) is utilized in the pumping action.

Figure 3:
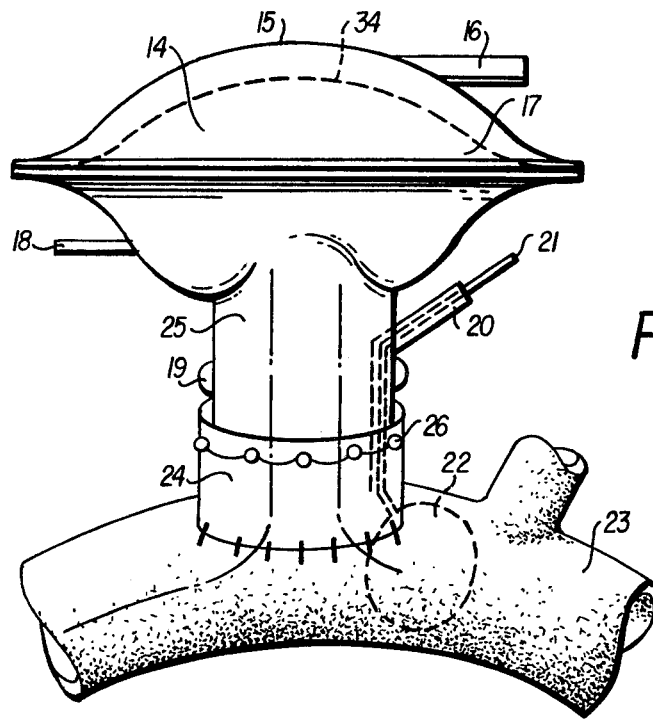
FIG. 3 illustrates the apparatus of FIG. 1 in greater detail.

FIG. 3 illustrates is greater detail the apparatus of FIG. 1. A Dacron ring 24 is sutured to the ascending main artery 23 and the connection 25 is made with the Dacron ring 24 by means of a tobacco pouch seam 26. A guide tube 20 extends through the connection 25 and towards the ascending main artery. A smaller tube 21 passes through the guide tube 20 to the control balloon 22 located in the artery. The smaller tube 21 serves as a pneumatic connection to the control balloon 22 to inflate and deflate the control balloon alternately to control the flow of blood through the artery. The guide tube 20 also provides means for inserting and withdrawing the control balloon 22 as required.

Figure 4:
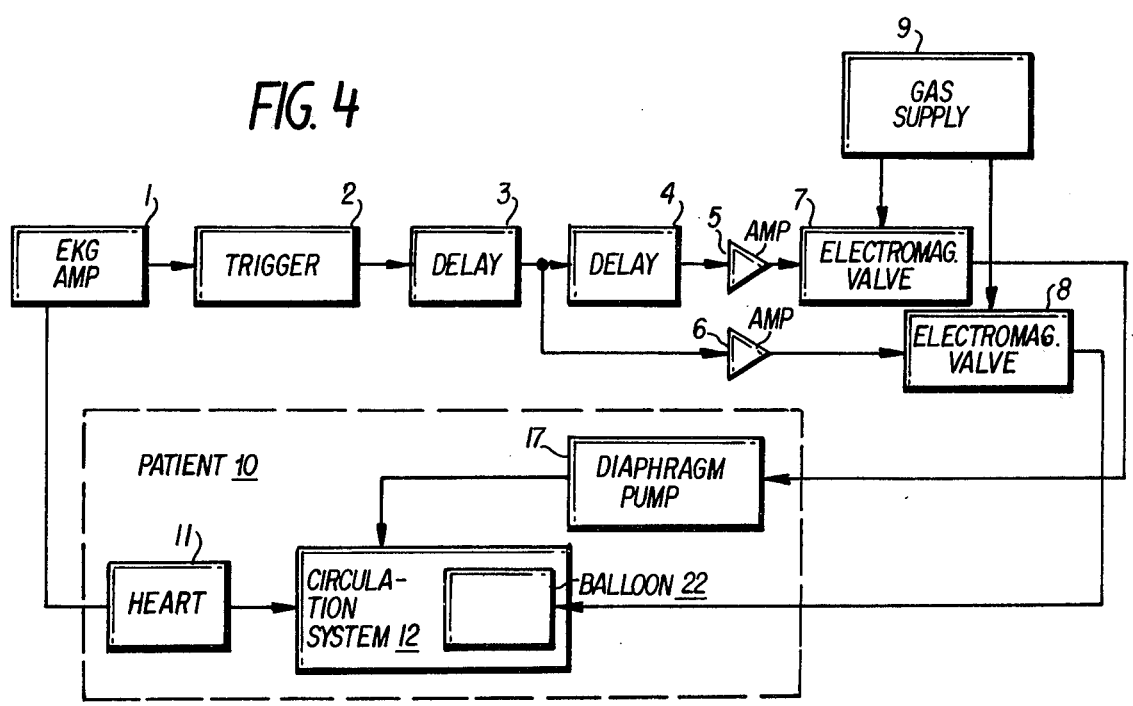
FIG. 4 illustrates schematically the control system for the apparatus of the present invention.

FIG. 4 diagrammatically illustrates the control system for synchronously operating the system. An EKG amplifier 1 is responsive to the pumping action of the heart 11. A trigger 2 is connected to the EKG amplifier 1 and operates two delaying elements 3 and 4 which in turn control amplifiers 5 and 6 respectively. The amplifiers 5 and 6 operate electromagnetic valves 7 and 8 controlling the flow of gas from supply 9. Valve 7 controls diaphragm pump 17 while valve 8 controls the balloon 22 located in the aorta 23 of the circulation system 12 of the patient 10.

The mechanical assist pump may be monitored by a pressure-measuring device connected at 18 and an electromagnetic flow meter 19 (see FIG. 3).

Figure 2:
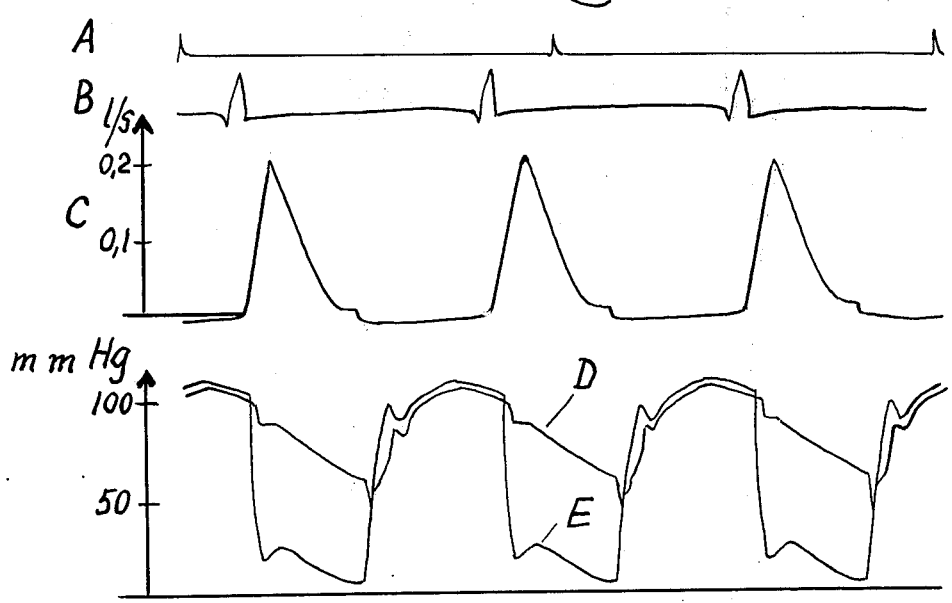
FIG. 2 is a schematic representation of curves measured in an electrical circuit simulating the employment of the apparatus according to the invention in a cardiovascular system.

FIG. 2 illustrates curves obtained in an electrical circulation model simulating the apparatus according to the present invention. In this figure:

A — the time pulses at one-second intervals of the recording,

B — the EKG simulated by the model,

C — the blood flow at the heart exit,

D — the pressure cycle in the central circulating system, and

E — the pressure cycle in the intermediate section between the heart exit and the variable resistance, i.e., the controlling balloon 22.

The system pressure is thus displaced in phase 180° as is the case in counterpulsation. During systole the pressure in the intermediate section is very low and principally depends upon the suction in the pumping chamber.

The apparatus is preferably applied by simultaneously introducing the controlling balloon 22 together with the connecting conduit 25 including the guide tube 20. For inactivating the system, the controlling balloon 22 needs merely be withdrawn into the connecting conduit 25, and the pumping chamber 17 as well as the balloon 22 is then pressurized. It will be appreciated that parameters such as the pressure in the circulating system can be measured via the guide tube 20. The apparatus can be removed by completely withdrawing the controlling balloon 22 and pinching off the connecting conduit 25. A pre-formed fracture or tear-off line may be incorporated in the connecting conduit 25 so that eventually only a very small piece of the connecting conduit 25 remains permanently in the body.

Figure 5:
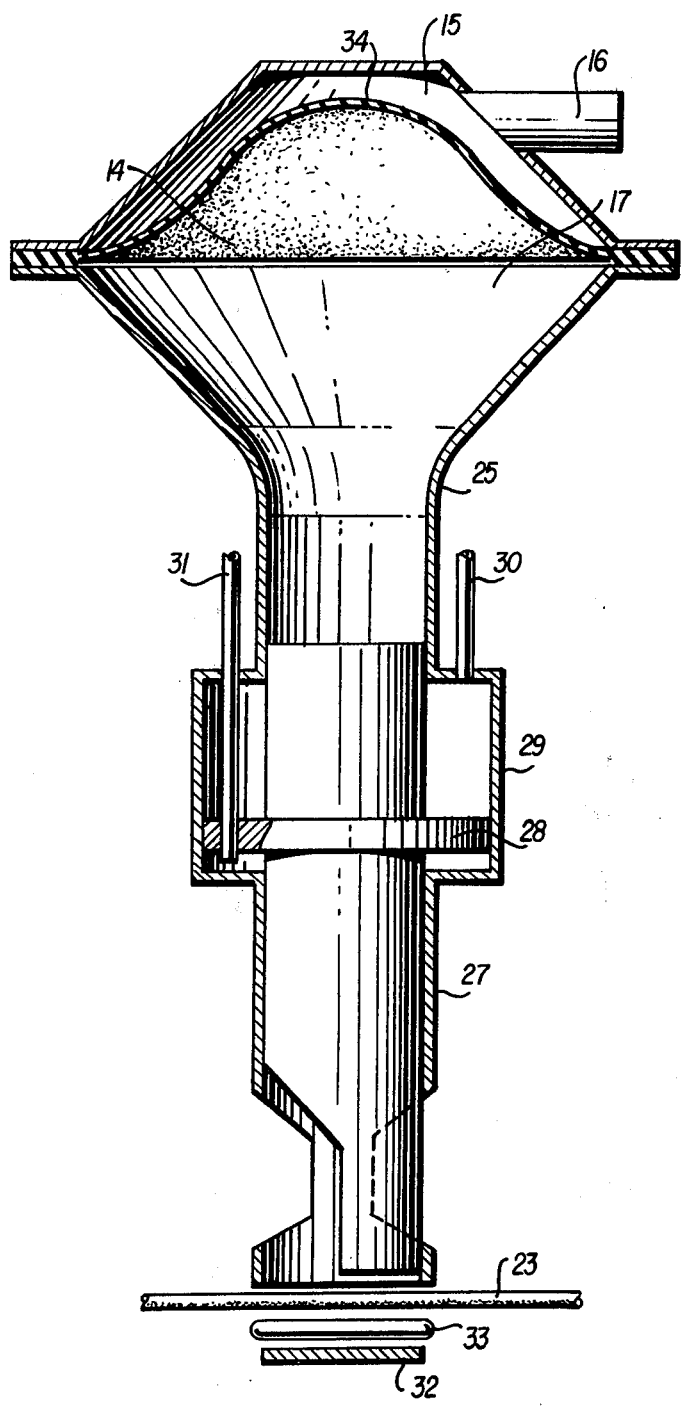
FIG. 5 illustrates a further embodiment of the present invention.

FIG. 5 illustrates a further embodiment of the invention wherein the control balloon 22 is replaced by a hydraulically or electromagnetically operated slide valve. In the conduit or pipe connection 25 there is an additional shiftable sliding pipe 27 which at its lower end is open on one side. Consequently, only the right opening of the pipe connection 25 is closed when the slide valve is closed. The left opening facing the heart always remains open. This corresponds to the action of the inflated control balloon 22.

An annular piston 28 is welded to the sliding pipe 27 and reciprocally moves in cylinder 29. Thus, the sliding pipe 27 may be operated hydraulically. Liquid under pressure is fed into the cylinder by way of pipe 30 causing the sliding pipe 27 to be pushed downwardly. The connecting pipe 31 extends downwardly through the cylinder 29 and a hole in the annular piston 28 so that upon fluid pressure being fed in through connecting pipe 31 the piston is caused to rise and the valve is opened. The connecting pipe 31 by passing through the annular piston 28 prevents the sliding pipe 27 from rotating.

In accordance with the invention, pressure is alternately applied to the two connecting pipes 30 and 31 respectively, synchronized with the heart beat. The control mechanism is the same as that illustrated in FIG. 4 and described above.

There is no special seal required between the annular piston 28 and the wall of the cylinder 29. Preferably, the piston is operated by an isotonic salt solution. To avoid thrombosis of the sliding valve it must be rinsed continuously with the salt solution, and consequently some leakage between the annular piston 28 and the wall of the cylinder 29 is required.

FIG. 5 also illustrates a convenient means for securing the wall of blood vessel 23 about the pipe connection 25. An annular inflatable member 33 is placed around the exterior surface of the pipe connection 25 with the wall of the blood vessel between the interior surface of the annular inflatable member 33 and the exterior surface of the pipe connection 25. A metal annular member 32 is positioned about the inflatable member 33 before the inflatable member 33 is inflated, thereby securing the wall of the blood vessel 23 without injury to the wall of the blood vessel.

The invention may be embodied in other specific forms without departing from the spirit or essential characteristics thereof. The embodiments disclosed are therefore to be considered in all respects as illustrative and not restrictive.

What is claimed is:

1. Apparatus for mechanically assisting circulation of the blood in the human body comprising:
   a. means defining a pumping chamber,
   b. a diaphragm extending across said chamber separating said chamber into first and second compartments,
   c. a first single conduit communicating with said second compartment for connection to the aorta of the human body whereby blood may flow between the aorta and said second compartment through said first conduit,
   d. a second conduit for connection to pneumatic means and communicating with said first compartment whereby air may be caused to flow into and out of said first compartment to move said diaphragm and cause blood to flow into and out of said second compartment, and
   e. variable resistance means extending through said first single conduit from said pumping chamber for positioning in the aorta downstream of the location in the aorta where said first single conduit is connected, said variable resistance means being arranged to periodically reduce blood flow through the aorta and simultaneously cause flow through said first single conduit into said second compartment.

2. Apparatus as defined in claim 1 wherein said variable resistance means is at least one valve.

3. Apparatus as defined in claim 1 wherein the variable resistance means is an inflatable controlling balloon.

4. Apparatus according to claim 3 further comprising a guide tube extending through the wall of said first single conduit and tube means extending through said guide tube to said controlling balloon to control the pneumatic inflation and deflation of said controlling balloon.

5. Apparatus as defined in claim 1 further comprising control means responsive to the rate of heart beat of a patient for controlling the operation of said pumping chamber and said variable resistance means.

6. Apparatus as defined in claim 1 further comprising a pipe member slidably mounted within said first single conduit, the end of said first single conduit being arranged to be inserted in the aorta and including at least two ports on opposite sides thereof respectively, the end of said sliding pipe member being arranged to close one of said ports when slid in one direction and to open said one port when slid in the opposite direction, and means for sliding said pipe member in opposite directions to control the flow of blood through the aorta.

7. Apparatus as defined in claim 6 wherein said means for sliding said sliding pipe member comprises a cylinder in said first single conduit and a piston mounted on said sliding pipe member and means for directing fluid into and out of opposite ends of said cylinder to control movement of said piston and sliding pipe member.

8. Apparatus as defined in claim 6 further comprising an inflatable annular member surrounding said first single conduit and a further annular member surrounding said inflatable annular member to secure the wall of the aorta about said first single conduit.

9. Apparatus for mechanically assisting circulation of the blood in the human body comprising:
   a. means defining a pumping chamber,
   b. a diaphragm extending across said chamber separating said chamber into first and second compartments,
   c. a first single conduit communicating with said second compartment for connection to the aorta of the human body whereby blood may flow between the aorta and said second compartment through said first conduit,
   d. a second conduit for connection to pneumatic means and communicating with said first compartment whereby air may be caused to flow into and out of said first compartment to move said diaphragm and cause blood to flow into and out of said second compartment,
   e. an inflatable controlling balloon for positioning the aorta downstream of the location in the aorta where said first single conduit is connected, said inflatable controlling balloon being arranged to periodically reduce blood flow through the aorta and simultaneously cause flow through said first single conduit into said second compartment,
   f. a guide tube extending through the wall of said first single conduit, and
   g. tube means extending through said guide tube to said controlling balloon to control the pneumatic inflation and deflation of said controlling balloon.

10. Apparatus as defined in claim 9 further comprising control means responsive to the rate of heart beat of a patient for controlling the operation of said pumping chamber and said inflatable controlling balloon.

11. Apparatus as defined in claim 9 further comprising a pipe member slidably mounted within said first single conduit, the end of said first single conduit being arranged to be inserted in the aorta and including at least two ports on opposite sides thereof respectively, the end of said sliding pipe member being arranged to close one of said ports when slid in one direction and to open said one port when slid in the opposite direction, and means for sliding said pipe member in opposite directions to control the flow of blood through the aorta.

12. Apparatus as defined in claim 11 wherein said means for sliding said sliding pipe member comprises a cylinder in said first single conduit and a piston mounted on said sliding pipe member and means for directing fluid into and out of opposite ends of said cylinder to control movement of said piston and sliding pipe member.

13. Apparatus as defined in claim 11 further comprising an inflatable annular member surrounding said first single conduit and a further annular member surrounding said inflatable annular member to secure the wall of the aorta about said first single conduit.

14. Apparatus for mechanically assisting circulation of the blood in the human body comprising:
   a. means defining a pumping chamber,
   b. a diaphragm extending across said chamber separating said chamber into first and second compartments,
   c. a first single conduit communicating with said second compartment for connection to the aorta of the human body whereby blood may flow between the aorta and said second compartment through said first conduit,
   d. a second conduit for connection to pneumatic means and communicating with said first compartment whereby air may be caused to flow into and out of said first compartment to move said diaphragm and cause blood to flow into and out of said second compartment, and e. a pipe member slidably mounted within said first single conduit, the end of said first single conduit being arranged to be inserted in the aorta and including at least two ports on opposite sides thereof respectively, the end of said sliding pipe member being arranged to close one of said ports when slid in one direction and to open said one port when slid in the opposite direction, and means for sliding said pipe member in opposite directions to control the flow of blood through the aorta.

15. Apparatus as defined in claim 14 wherein said means for sliding said sliding pipe member comprises a cylinder in said first single conduit and a piston mounted on said sliding pipe member and means for directing fluid into and out of opposite ends of said cylinder to control movement of said piston and sliding pipe member.

16. Apparatus as defined in claim 14 further comprising an inflatable annular member surrounding said first single conduit and a further annular member surrounding said inflatable annular member to secure the wall of the aorta about said first single conduit.

17. Apparatus as defined in claim 14 further comprising variable resistance means for positioning in the aorta downstream of the location in the aorta where said first single conduit is connected, said variable resistance means being arranged to periodically reduce blood flow through the aorta and simultaneously cause flow through said first single conduit into said second compartment.

18. Apparatus as defined in claim 17 wherein said variable resistance means is at least one valve.

19. Apparatus as defined in claim 17 wherein the variable resistance means is an inflatable controlling balloon.

20. Apparatus as defined in claim 17 wherein said variable resistance means extends through the first single conduit to the pumping chamber.

21. Apparatus according to claim 19 further comprising a guide tube extending through the wall of said first single conduit and tube means extending through said guide tube to said controlling baloon to control the pneumatic inflation and deflation of said controlling balloon.

22. Apparatus as defined in claim 17 further comprising control means responsive to the rate of heart beat of a patient for controlling the operation of said pumping chamber and said variable resistance means.

* * * * *